United States Patent
Shanghvi et al.

(10) Patent No.: US 10,102,625 B2
(45) Date of Patent: Oct. 16, 2018

(54) METHOD AND SYSTEM FOR ANALYZING ONE OR MORE MULTI-RESOLUTION MEDICAL IMAGES

(71) Applicant: ADITYA IMAGING INFORMATION TECHNOLOGIES (AIIT), Mumbai (IN)

(72) Inventors: Umesh Shanghvi, Mumbai (IN); Rhushabh Goradia, Mumbai (IN); Adarsh Jain, Mumbai (IN)

(73) Assignee: ADITYA IMAGING INFORMATION TECHNOLOGIES (AIIT), Mumbai (IN)

( * ) Notice: Subject to any disclaimer, the term of this patent is extended or adjusted under 35 U.S.C. 154(b) by 69 days.

(21) Appl. No.: 15/506,676

(22) PCT Filed: Aug. 31, 2015

(86) PCT No.: PCT/IN2015/000337
§ 371 (c)(1),
(2) Date: Feb. 24, 2017

(87) PCT Pub. No.: WO2016/035094
PCT Pub. Date: Mar. 10, 2016

(65) Prior Publication Data
US 2017/0330318 A1    Nov. 16, 2017

(30) Foreign Application Priority Data
Sep. 1, 2014  (IN) .......................... 2778/MUM/2014

(51) Int. Cl.
G06K 9/00       (2006.01)
G06T 7/00       (2017.01)
(Continued)

(52) U.S. Cl.
CPC ............ G06T 7/0012 (2013.01); A61B 6/463 (2013.01); A61B 8/463 (2013.01);
(Continued)

(58) Field of Classification Search
None
See application file for complete search history.

(56) References Cited

U.S. PATENT DOCUMENTS 9,836,865 B2 * 12/2017 Dobson .................. G06T 11/60
2006/0127880 A1 * 6/2006 Harris ................ G06K 9/00127
435/4
(Continued)

OTHER PUBLICATIONS

International Search Report and Written Opinion received in counterpart PCT Application No. PCT/IN2015/000337, dated Feb. 8, 2016, 8 pages.
Kulkarni et al., "Multiresolution Analysis for Medical Image Segmentation Using Wavelet Transform," International Journal of Emerging Technology and Advanced Engineering, pp. 543-545, vol. 4, Issue 6, Jun. 2014, 3 pages.
(Continued)

*Primary Examiner* — Shervin Nakhjavan
(74) *Attorney, Agent, or Firm* — Klarquist Sparkman, LLP (57) ABSTRACT

A method and system analyzes multi-resolution medical images. The method includes receiving one or more multi-resolution medical images of one or more tissues. Each multi-resolution medical image is divided into a plurality of segments. Thereafter, each segment of the plurality of segments of each multi-resolution medical image is processed in parallel, utilizing one or more computation nodes, wherein each computation node includes one or more Graphical Processing Units (GPUs). The results corresponding to each segment of a multi-resolution medical image are collated, and a collated report is displayed.

13 Claims, 9 Drawing Sheets

(51) Int. Cl.
*A61B 6/00* (2006.01)
*A61B 8/00* (2006.01)

(52) U.S. Cl.
CPC ..... *G06K 9/00127* (2013.01); *G06K 9/00986* (2013.01); *G06T 2207/20021* (2013.01)

(56) References Cited

U.S. PATENT DOCUMENTS

| | | | |
|---|---|---|---|
| 2006/0159367 A1* | 7/2006 | Zeineh | G02B 21/365 382/276 |
| 2008/0150937 A1* | 6/2008 | Lundstrom | G06T 15/005 345/419 |
| 2010/0303348 A1 | 12/2010 | Tolliver et al. | |
| 2012/0163681 A1* | 6/2012 | Lohse | G01N 21/6428 382/128 |
| 2013/0223716 A1* | 8/2013 | Mori | A61B 5/0013 382/131 |
| 2014/0314286 A1* | 10/2014 | Madabhushi | G06T 7/0012 382/128 |

OTHER PUBLICATIONS

Extended European Search Report of counterpart European Patent Application No. 15838790.2, dated May 4, 2018, 9 pages.

Teodoro et al., "Coordinating the use of GPU and CPU for improving performance of compute intensive applications," *Cluster Computing and Workshops, 2009, Cluster '09, IEEE International Conference on, IEEE, Piscataway, NJ*, Aug. 31, 2009, pp. 1-10, 10 pp.

Teodoro et al., "High-throughput Analysis of Large Microscopy Image Datasets on CPU-GPU Cluster Platforms," *Parallel & Distributed Processing (IPDPS) 2013 IEEE 27th International Symposium on IEEE*, May 20, 2013, pp. 103-114, 12 pages.

Qi et al., "Gpu Enabled Parallel Touching Cell Segmentation Using Mean Shift Based Seed Detection and Repulsive Level Set," *High Performance Computing (HP) Workshop associated with Proc. International Conference on Medical Image Computing and Computer Assisted Intervention (MICCAI)*, Sep. 24, 2010, retrieved from: http://pleiad.umdnj.edu/Cvii/pdfs/hpmiccai_2010_cell.pdf, 10 pages.

* cited by examiner

METHOD AND SYSTEM FOR ANALYZING ONE OR MORE MULTI-RESOLUTION MEDICAL IMAGES

CROSS REFERENCE TO RELATED APPLICATIONS

This is the U.S. National Stage of International Application No. PCT/IN2015/000337, filed Aug. 31, 2015, which was published in English under PCT Article 21(2), which in turn claims the benefit of India Application No. 2778/MUM/2014, filed Sep. 1, 2014. Both applications are incorporated herein by reference.

FIELD OF THE INVENTION

The invention generally relates to the field of analyzing medical images of tissue. More specifically, the invention relates to a method and system of quick analysis of histo-pathology medical images of stained animal tissues using a cluster of Graphical Processing Units (GPUs) for pre-clinical trial data.

BACKGROUND OF THE INVENTION

In digital pathology, images of a tissue are presented to a pathologist for evaluation. The consistency of diagnosis by different pathologists may significantly improve if computer algorithms are used to assist the pathologists. Generally, a process of automatically analyzing an image of a tissue using computer algorithms is a time consuming process. There are situations when a user loads plurality of images of tissues at a time for analysis. Typically, analysis of a plurality of multi-resolution images simultaneously is a time consuming process. Each medical image is executed as a job one at a time. Further, each processing unit may have heavy workload at a time if the plurality of medical images is queued up on the same processing unit.

In light of the above, there is a need for an improved method and system for quickly analyzing medical images of a tissue.

BRIEF DESCRIPTION OF FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the invention.

FIG. 7 (a, left) depicts a tile of the multi-resolution medical image at 2.5× (image resolution) made up of n×n pixels and FIG. 7 (a, right) depicts 16 corresponding tiles at 10× of the same tissue region as represented by the 2.5× tile.

FIG. 7 (b) depicts a single 10× tile expanded to 16 tiles at 40×.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION OF THE INVENTION

Before describing in detail embodiments that are in accordance with the invention, it should be observed that the embodiments reside primarily in method steps and system components related to analysis of medical images of a tissue for pre-clinical trial data.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article or composition that comprises a list of elements does not include only those elements but may include other elements not expressly listed or inherent to such process, method, article or composition. An element proceeded by "comprises . . . a" does not, without more constraints, preclude the existence of additional identical elements in the process, method, article or composition that comprises the element.

Generally speaking, pursuant to various embodiments, the invention provides a method and system for analyzing histo-pathology medical images of stained animal tissues using Graphical Processing Units (GPUs) for pre-clinical trial data. The method and system analyzes a single medical image at multiple resolutions using GPUs for computing effects of administered drugs on the animal tissue.

A GPU is an add-on accelerator card which is controlled by a host Central Processing Unit (CPU). The GPU includes an on-board memory which is utilized to perform a job. There is a connection arrangement between the host CPU, system RAM and a GPU card. The GPU card includes a set of Arithmetic Logic Units (ALUs) to perform computations and memory to store data relevant for computations. The interconnection between the host CPU and the GPU are through Peripheral Component Interconnect express (PCIe) bus. The host CPU is configured to transfer relevant data from Random Access Memory (RAM) to GPU's memory. The relevant data can be transferred asynchronously along with ongoing GPU computations while the GPU is busy computing on the current data. The host CPU can make sure the next set of data is transferred from RAM to GPU memory and ready for execution before the execution on the current data is completed by the GPU.

There are hardware pipes available to transfer data to GPUs. Thus, parallel transfers of data from RAM to the GPU memory are performed through the hardware pipes using streams.

Figure 1:
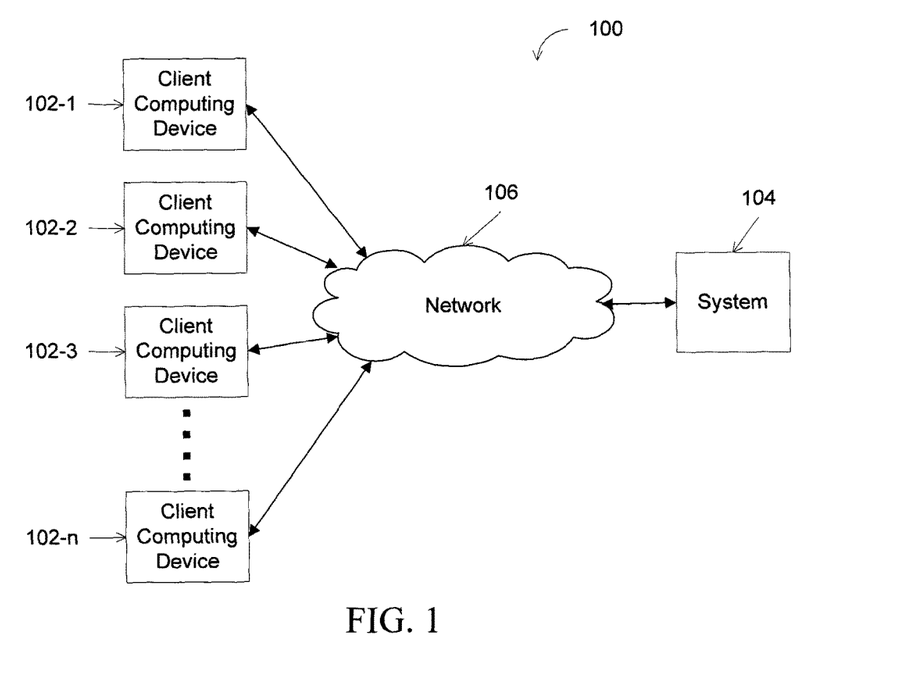
FIG. 1 illustrates a computing environment that performs analysis of one or more multi-resolution medical images in accordance with an embodiment of the invention.

FIG. 1 illustrates a computing environment that performs analysis of one or more multi-resolution medical images in accordance with an embodiment of the invention. As illustrated, one or more client computing devices 102(1-n) communicates with a system 104 via a network 106. Network 106 can be for example, but not limited to, a Local Area Network (LAN), a Metropolitan Area Network (MAN), a Wide Area Network (WAN), and a Wireless LAN (WLAN). System 104 receives one or more multi-resolution medical images of a tissue for analyzing from one or more clients computing devices 102(1-n). A client computing device 102-1 can be for example, but not limited to, a desktop computer, a laptop, a personal digital assistant (PDA), a tablet and a mobile phone.

Client computing device 102-1 makes a request to process and analyze one or more multi-resolution medical images. While making a request, a user may upload the one or more multi-resolution medical images or specify a storage location for system 104 to retrieve the one or more multi-resolution medical images. Further, the user may associate a priority with each multi-resolution medical image. Accordingly, system 104 queues up a job for each multi-resolution medical image submitted by client computing device 102-1 and provides periodic job updates to client computing device 102-1 till the completion of the job.

Figure 2:
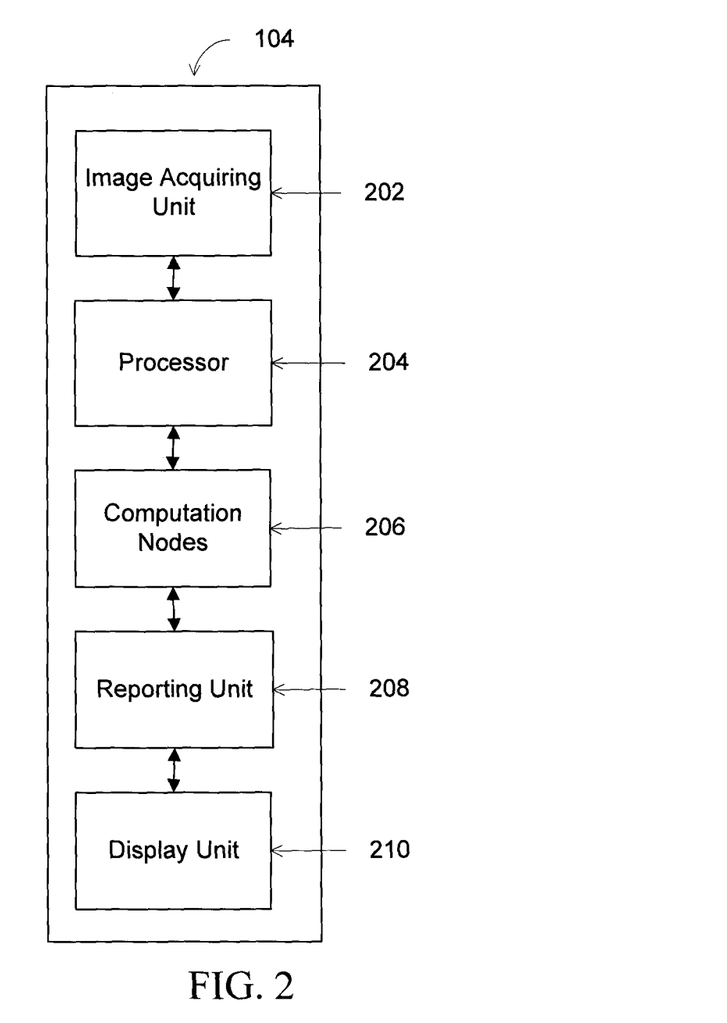
FIG. 2 illustrates a block diagram of a system for analyzing one or more multi-resolution medical images in accordance with an embodiment of the invention.

FIG. 2 illustrates a block diagram of system 104 for analyzing one or more multi-resolution medical images in accordance with an embodiment of the invention.

System 104 includes an image acquiring unit 202 which receives one or more multi-resolution medical images of one or more tissues, wherein the tissue is a stained tissue that is treated with one or more drugs. Image acquiring unit 202 receives the one or more multi-resolution medical images from one of, but not limited to, a scanning device, an archived storage and one or more client computing devices 102(1-n). Image acquiring unit 202 is communicatively coupled with one of or more of, but not limited to, the scanning device, the archived storage and one or more client computing devices 102(1-n) over network 106.

Image acquiring unit 202 hands over the one or more multi-resolution medical images to a processor 204 for initiating the analysis of the one or more multi-resolution medical images. Processor 204 divides each multi-resolution medical image into a plurality of segments, wherein each segment includes one or more tiles.

In order to effectively and efficiently perform the analysis, processor 204 creates a sub-job for each segment of the multi-resolution medical image. A sub-job performs the analysis of one or more tiles associated with a segment across multiple resolutions of the same section of a tissue region represented by the segment associated with the multi-resolution medical image. Accordingly, processor 204 queues up each sub-job into a global job array for scheduling the processing of each sub-job. Processor 204 schedules each sub-job at one or more computation nodes 206(1-n) using the global job array. Processor 204 schedules each sub-job at one or more computation nodes 206(1-n) based on a priority associated with each sub-job and an availability status of each computation node.

In an embodiment, processor 204 divides each sub job into a plurality of sub-sub-jobs. A sub-sub-job performs an analysis of one or more tiles of a segment at an image resolution of the multiple resolutions associated with the multi-resolution medical image on a GPU. Therefore, for processing a sub-job, processor 204 schedules each sub-sub-job at a GPU on a computation node 206(1-n) based on a priority associated with each sub-job and an availability status of each computation node. In an embodiment, each sub-sub-job run in parallel with other sub-sub-jobs on the same GPU associated with the same parent sub-job.

Upon receiving a sub-job, a computation node of one or more computation nodes 206(1-n) performs an analysis of one or more tiles of a segment at an image resolution of the multiple resolutions associated with the multi-resolution medical image. In an embodiment, each computation node includes one or more Graphical Processing Units (GPUs). Accordingly, one or more GPUs of a computation node perform an analysis of the one or more tiles of the segment at an image resolution. Thereafter, reporting unit 208 collates results corresponding to each segment of a multi-resolution medical image.

In an embodiment, reporting unit 208 collates analysis results corresponding to each sub-sub-job of a sub job corresponding to a segment of a multi-resolution medical image. Further, reporting unit 208 collates analysis results corresponding to each sub-job corresponding to each segment of the multi-resolution medial image in response to collating analysis results corresponding to each sub-sub-job of each sub-job. After collating, reporting unit 208 generates a collated report based on analysis results corresponding to each sub-job corresponding to each segment of the multi-resolution medial image.

Once the collated report is generated, a display unit 210 displays the collated report corresponding to the multi-resolution image.

Figure 3:
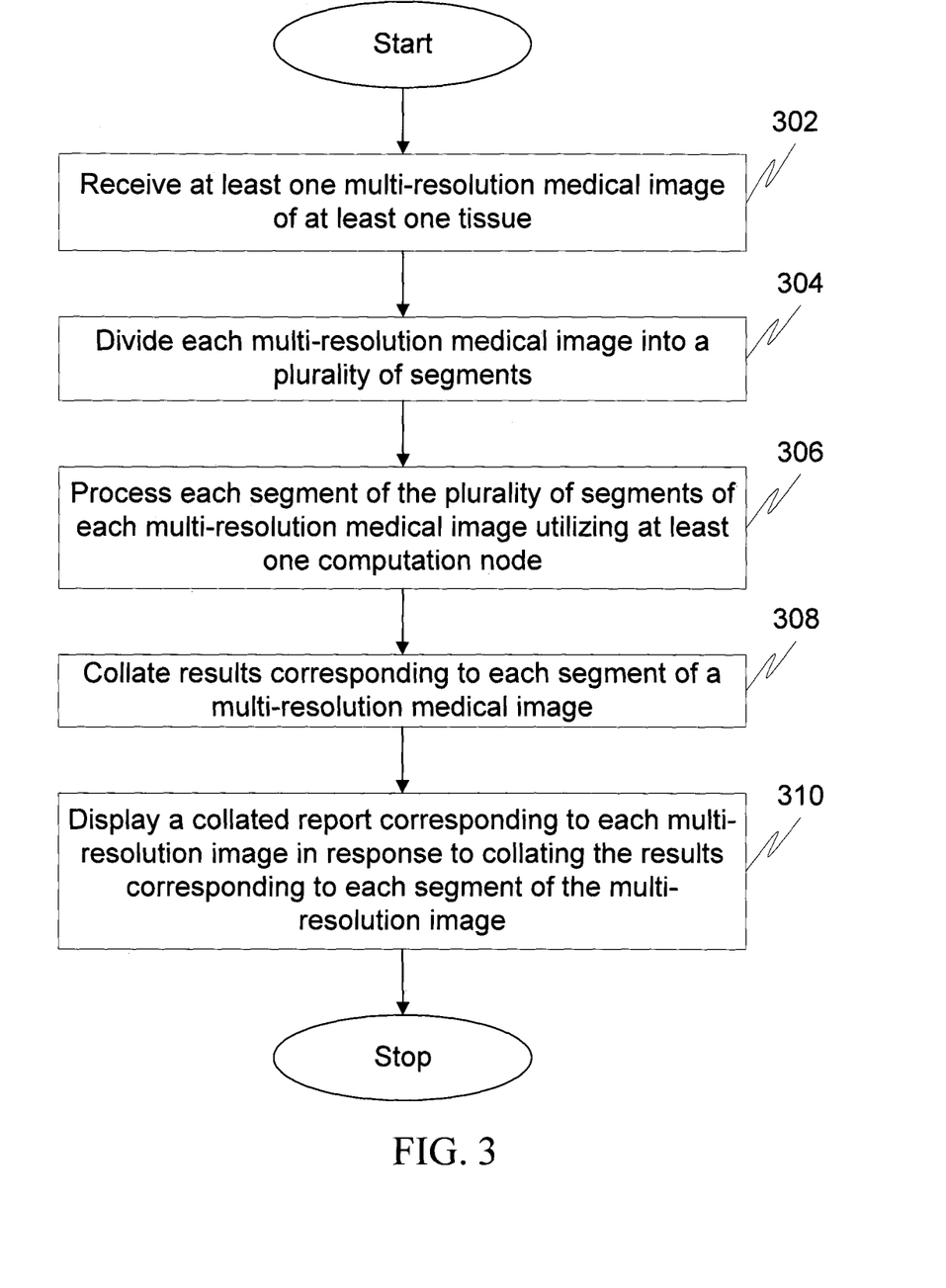
FIG. 3 illustrates a flow chart of a method for analyzing one or more multi-resolution medical images in accordance with an embodiment of the invention.

FIG. 3 illustrates a flow chart of a method for analyzing one or more multi-resolution medical images in accordance with an embodiment of the invention.

During histopathological preclinical trials, an animal such as rat is tested with one or more drugs to evaluate the effect of the one or more drugs. The one or more drugs are administered into the animal and a target organ of the animal is evaluated for the one or more drugs. The effect of the one or more drugs on the target organ is evaluated by analyzing images of stained tissues of the target organ.

In order to begin the analysis process, image acquiring unit 202 receives one or more multi-resolution medical images of a tissue at step 302. The tissue is a stained tissue that is treated with one or more drugs. The type of the tissue can be one of, but not limited to, liver, muscle, uterus, heart, fat tissue, gastrointestinal tissue, lung, renal, stomach, skin, thyroid, lymph node, bone, pancreas, spleen, eye, ovary, and central nervous system.

Moving on, at step 304, processor 204 divides each multi-resolution medical image into a plurality of segments. Each segment includes one or more tiles. For example, a segment may consists of 2 tiles for analysis at one image resolution and the same segment is divided into 16 tiles for analysis at another image resolution but representing the same tissue region. Processor 204 schedules analysis of the plurality of segments on one more computation nodes 206 (1-n).

Accordingly, at step 306, a computation node 206-1 processes a segment of the plurality of segments of a multi-resolution medical image. Step 306 is further described in detail in conjunction with FIG. 4.

Figure 5:
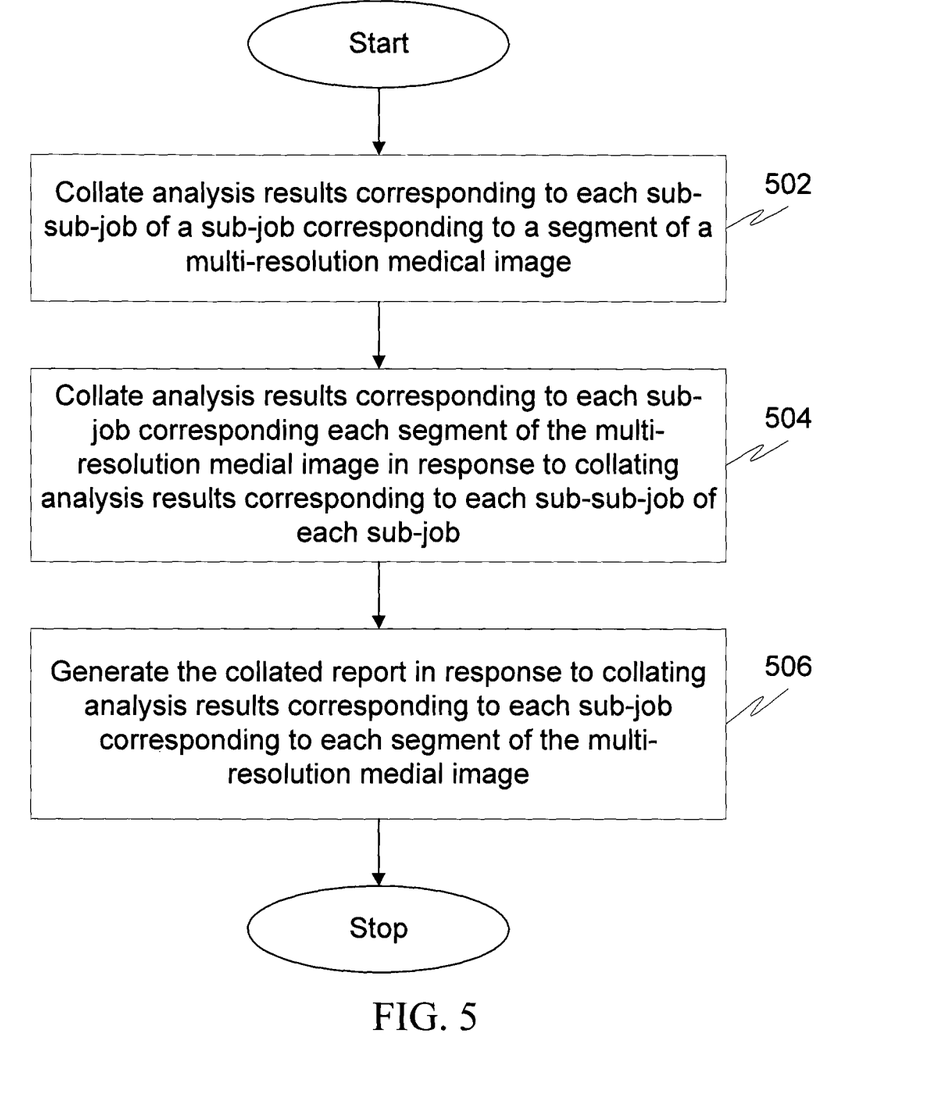
FIG. 5 illustrates a flow chart of a method of collating results corresponding to each segment of a multi-resolution medical image in accordance with an embodiment of the invention.

Once the analysis of each segment is done, reporting unit 208 collates results corresponding to each segment of a multi-resolution medical image from each GPU of one or more computation nodes 206 (1-*n*) at step 308, the process is further described in detail in conjunction with FIG. 5.

Finally, at step 310, display unit 210 displays a collated report corresponding to the multi-resolution image based on collated results corresponding to each segment of the multi-resolution image. The collated report can be archived for future viewing references.

Figure 4:
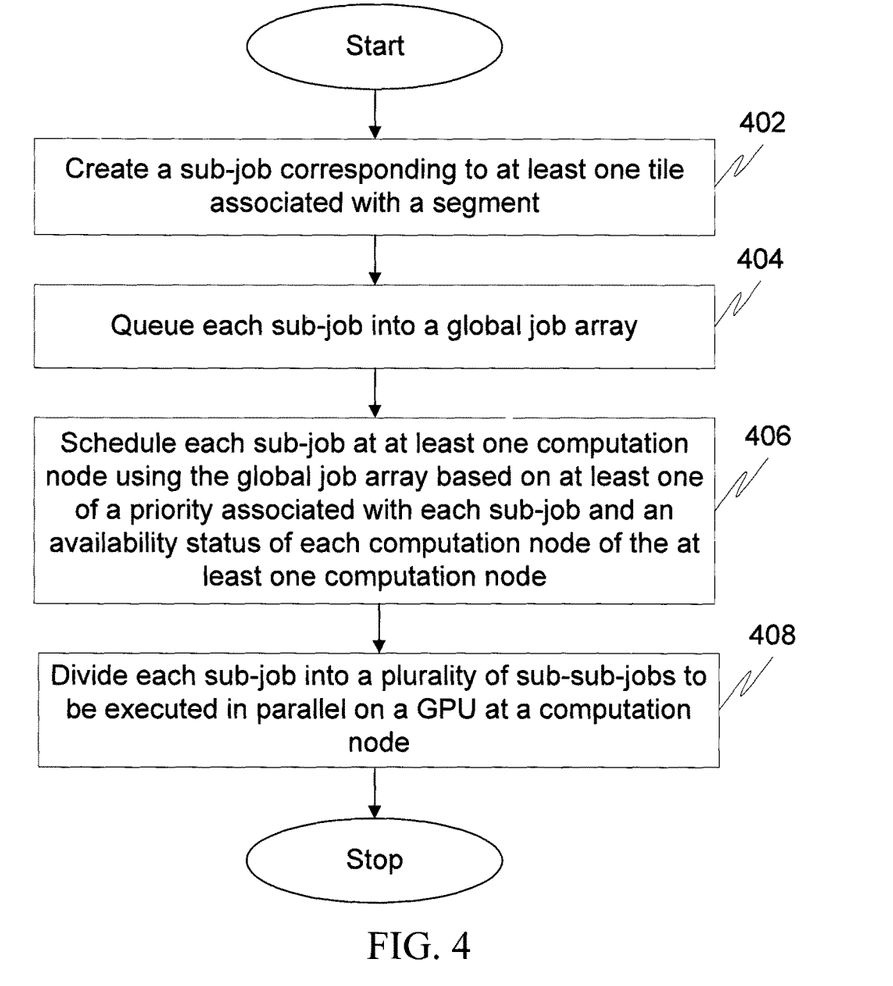
FIG. 4 illustrates a flow chart of a method of processing each segment of a plurality of segments of each multi-resolution medical image utilizing one or more computation nodes in accordance with an embodiment of the invention.

FIG. 4 illustrates a flow chart of a method of processing each segment of the plurality of segments of each multi-resolution medical image utilizing one or more computation nodes 206(1-*n*) in accordance with an embodiment of the invention.

At step 402, a sub-job corresponding to a segment of a multi-resolution medical image is created. A sub-job corresponds to analyzing one or more tiles associated with the segment across multiple image resolutions associated with the multi-resolution medical image. For example, a sub-job corresponds to analysis of 2 tiles of a segment of a multi-resolution medical image at 2.5× (image resolution), 16 tiles of a single 2.5× tile of the same segment at 10× (32 tiles at 10× for 2 tiles at 2.5×) and 256 tiles of a single 2.5× tile of the same segment at 40× (512 tiles at 40× for 2 tiles at 2.5×).

At step 404, each sub-job is queued into a global job array for scheduling a sub-job. Accordingly, each sub job is scheduled at a GPU at one or more computation nodes using the global job array at step 406. The scheduling of each sub-job depends on one of a priority associated with each sub-job and an availability status of each computation node.

At step 408, each sub-job is divided into a plurality of sub-sub-jobs, wherein a plurality of sub-sub-jobs of a sub-job are executed in parallel on a GPU at a computation node. A sub-sub-job corresponds to analyzing one or more tiles of the segment at an image resolution of the multiple resolutions associated with the multi-resolution medical image. Each sub-sub-job corresponding to a multi-resolution medical image is executed in a predefined order based on a type of the tissue in the multi-resolution medical image. For example, a rat's kidney requires to be processed at 40× tiles of a sub-job before the corresponding parent 10× tiles and grandparent 2.5× tiles. However, the order might vary for rat's liver tissues or so for any other organ slides.

FIG. 5 illustrates a flow chart of a method of collating results corresponding to each segment of a multi-resolution medical image in accordance with an embodiment of the invention.

At step 502, analysis results corresponding to each sub-sub-job of a sub-job corresponding to a segment of a multi-resolution medical image are collated. The analysis results for each sub-sub-job are collated at a GPU of the one or more computation nodes 206(1-*n*).

At step 504, analysis results corresponding to each sub-job corresponding to each segment of the multi-resolution medial image are collated after collating the analysis results corresponding to each sub-sub-job of each sub-job.

At step 506, the collated report is generated based on collated analysis results corresponding to each sub-job corresponding to each segment of the multi-resolution medial image.

Figure 6:
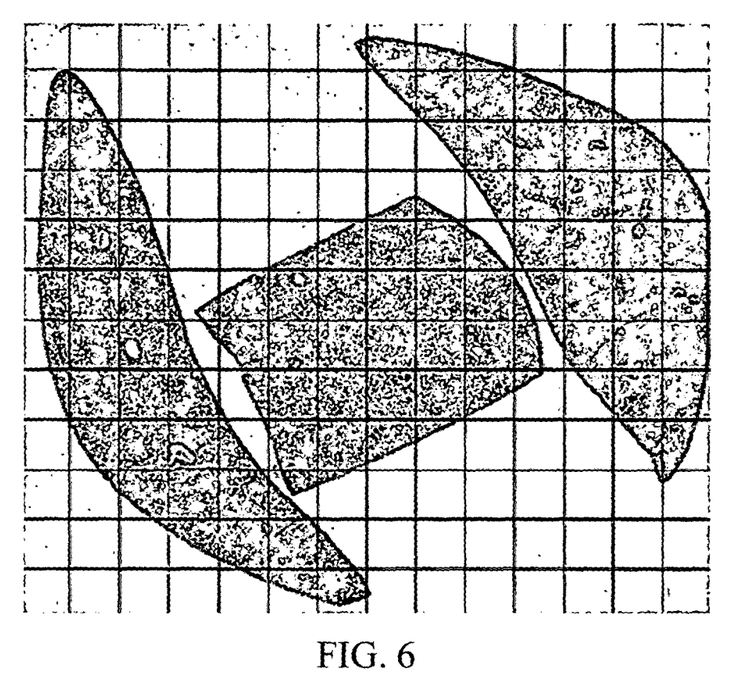
FIG. 6 depicts a sample of a multi-resolution medical image of a stained tissue of a rat's liver.

FIG. 6 depicts a sample of a multi-resolution medical image of a stained tissue of a rat's liver. In accordance with an exemplary embodiment of the invention, image acquiring unit 202 receives the multi-resolution image to be analyzed for histopathological pre-clinical trials.

An analysis job corresponding to the multi-resolution medical image is placed in a queue. Any existing workload managers and job schedulers can be used for scheduling the analysis job in system 104. A workload manager and a job scheduler submit an analysis job to system 104 based on a priority associated with the analysis job.

Once the analysis job is submitted to system 104, processor 204 initiates the execution of the analysis job. Accordingly, processor 204 segments the multi-resolution medical image into a plurality of segments, wherein each segment includes one or more tiles. In FIG. 6, each blue square signifies a segment of the multi-resolution medical image which is called as a tile. In an exemplary embodiment, each tile is of 512×512 pixels.

Processor 204 creates a sub-job corresponding to a set of segments of the multi-resolution medical image. A sub-job corresponds to analyzing one or more tiles of the multi-resolution medical image across multiple resolutions of the multi-resolution of medical image.

Figure 7:
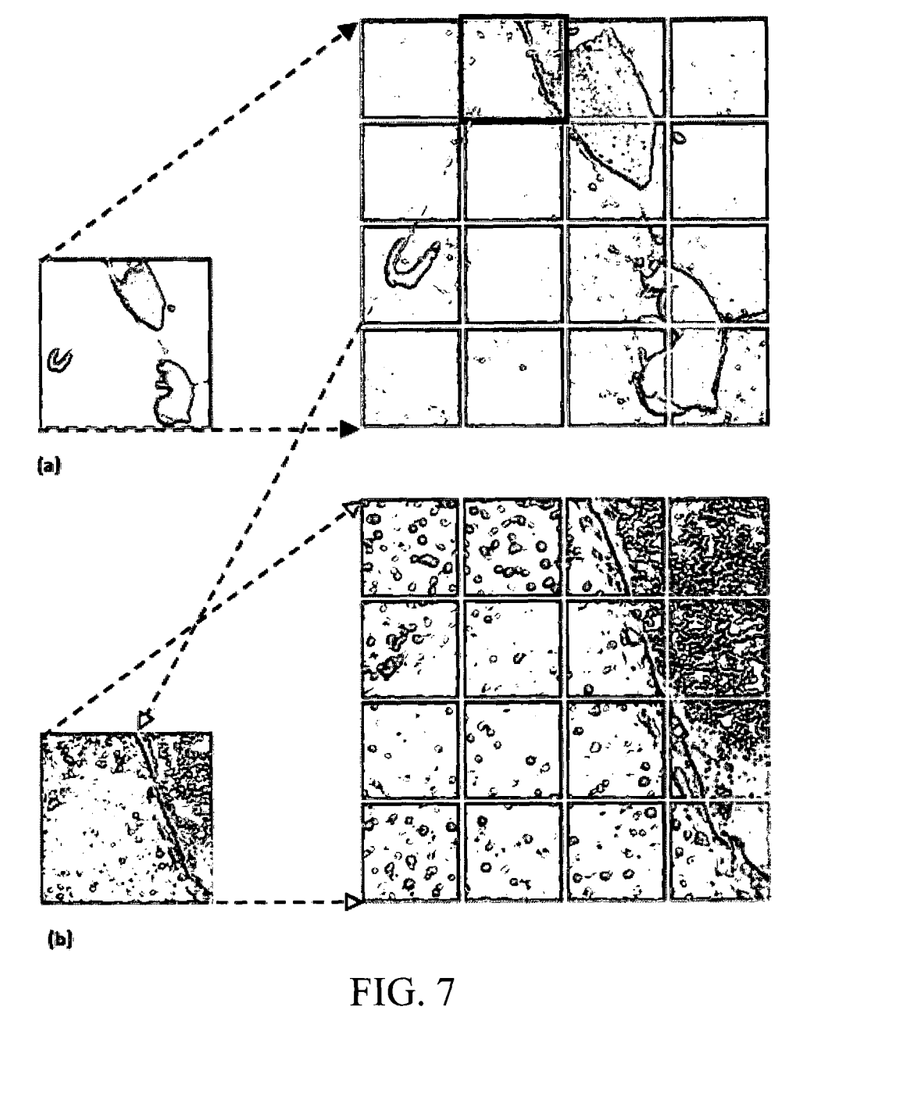

FIG. 7 (*a*, left) depicts a tile of the multi-resolution medical image at 2.5× (image resolution) made up of n×n pixels and FIG. 7 (*a*, right) depicts 16 corresponding tiles at 10× of the same tissue region as represented by the 2.5× tile. The same segment of the multi-resolution medical image can be represented with 4n×4n pixels at 10× (since 10×=4 times 2.5×). Thus, there are 16 tiles of n×n resolution at 10× representing the same segment of the multi-resolution medical image at 2.5×, which is represented in FIG. 7 (*a*). Similarly, FIG. 7 (*b*) depicts a single 10× tile expanded to 16 tiles at 40×.

Figure 8:
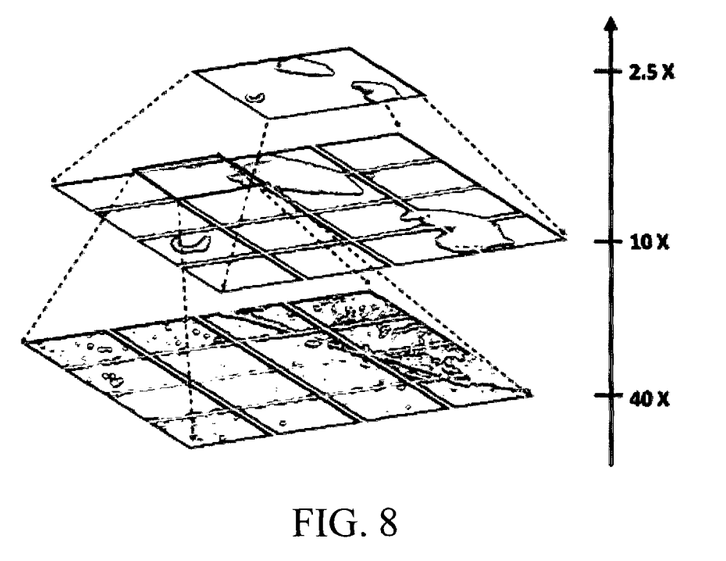
FIG. 8 depicts a tile pyramid showing a 2.5× tile of a segment of the multi-resolution medical image getting expanded to 10×, and the tile pyramid corresponding to a 10× tile representing part of the same segment getting expanded to corresponding sixteen tiles of 40×.

FIG. 8 depicts a tile pyramid showing a 2.5× tile of a segment of the multi-resolution medical image getting expanded to 10×, and the tile pyramid corresponding to a 10× tile representing part of the same segment getting expanded to corresponding sixteen tiles of 40×. Thus, 256 tiles at 40× correspond to 16 tiles at 10×. 16 tiles at 40× of a 10× tile is shown as the base of the tile pyramid. A part of a segment of the multi-resolution medical image which is represented as a tile (blue squares in FIG. 6) at 2.5× can be represented by 16 tiles at 10× (10× is 4 times 2.5×) and 256 tiles at 40×. For example, in FIG. 7*a*, FIG. 7*b* and FIG. 8, a 10× image is a 4× up-sampled version of a 2.5× image i.e. section of tissue corresponding to one tile of 2.5× is represented by 16 tiles at 10×. Similarly, a tile of the multi-resolution medical image at 10× corresponds to 16 tiles at 40× representing the same segment of the multi-resolution medical image. As higher the resolution, more details are visible.

In accordance with an embodiment of the invention, a sub-job analyzes a set 'S' of tiles across image resolutions, where if set 'S' contains 1 tile of 2.5× (S=1|2.5×), then the sub job corresponds to analyzing 1 tile of 2.5×, 16 tiles of 10× representing the same segment of the multi-resolution medical image as represented by the 2.5× tile (Refer to FIG. 7*a* and FIG. 7*b*) and 256 tiles at 40× representing the same segment of the multi-resolution medical image (Refer to FIG. 8). Thus, a sub-job consists of a set of two tiles at 2.5×, 32 corresponding tiles of 10× and 512 corresponding tiles of 40×, all representing the same segment of the multi-resolution medical image. A sub-job essentially signifies a smaller workload of the job to be executed in parallel with other sub-jobs.

Thereafter, processor 204 queues up sub-jobs corresponding to different tiles of the multi-resolution medical image in a global job array. Each sub-job is scheduled at one or more computation nodes 206(1-n). A sub-job is scheduled based on the priority associated with the sub-job in the global job array and availability of computation nodes. Each computation node includes one or more Graphical Processing Units (GPUs). Each sub-job is executed on a GPU of one or more computation nodes 206(1-n). There can be "m" sub-jobs on "n" GPUs, where m is greater than, equal to or less than n.

Each sub-job is divided into a plurality of sub-sub-jobs. Each sub-sub-job analyzes one or more tiles of the segment at an image resolution. For example, 32 tiles of a segment of the multi-resolution medical image are analyzed at 10× image resolution and 512 tiles of the same segment are analyzed at 40× image resolution through different sub-sub-jobs of the parent sub-job. In the above example, if 32 sub-sub-jobs are created, each sub-sub-job analyzes 1 tile of 10× and corresponding 16 tiles of 40×.

Figure 9:
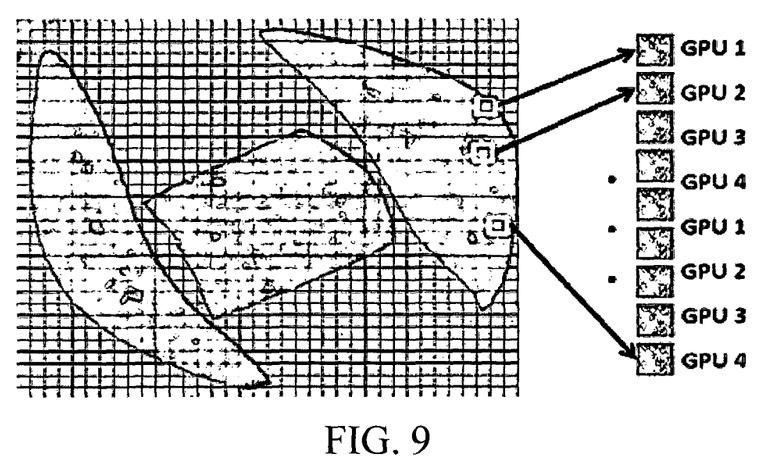
FIG. 9 depicts multiple GPUs that are utilized to compute multiple sub-jobs simultaneously.

In an exemplary embodiment of the invention, a sub-sub-job is executed on a GPU using Compute Unified Device Architecture (CUDA) streams. While executing a sub-sub-job on a GPU, the same segment of the multi-resolution medical image is executed on one image resolution after another i.e. each tile corresponding to current sub-sub-job is processed for a particular resolution before moving onto the next image resolution in that sub-job. For example for rat's liver, two tiles of 2.5× in a sub-job is transferred and processed using 2 sub-sub-jobs, followed by 32 tiles of 10× and then 512 tiles of 40× of the same segment of the multi-resolution medical image using 32 sub-sub-jobs (FIG. 7a, FIG. 7b and FIG. 8). Thus, two streams are utilized for transferring and processing 2.5× tiles, all 32 streams are utilized for 10× and again, all 32 streams are utilized for transferring and processing of 512 tiles of 40× (16 tiles of 40× per stream). Each stream is utilized in parallel by the corresponding sub-sub-job. Thus, multiple tiles are analyzed in parallel in various streams. FIG. 9 depicts multiple GPUs that are utilized to compute multiple sub-jobs simultaneously.

Figure 10:
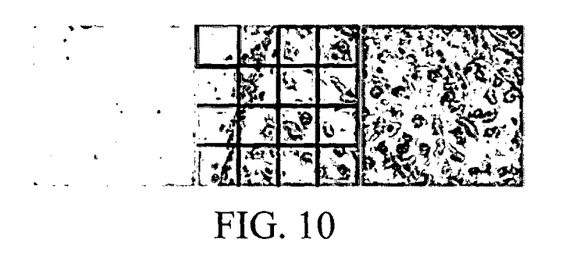
FIG. 10 shows three example tiles of the multi-resolution medical image at 10×.

In accordance with an embodiment of the invention, one or more tiles which do not contain any portion of tissue are not processed. FIG. 10 shows three example tiles of the multi-resolution medical image at 10×. The tile on the left contains only the background glass image while the middle and the right tiles contain the tissue. The middle and the right tiles are processed for analysis of features at 10×, but not the tile to the left. A representative segmentation showing 16 tiles of 40× is shown for the middle 10× tile. Although the 10× tile in the middle contains tissue, all the corresponding 40× children tiles does not contain tissue regions. For example, top-left 40× tile (represented by a green box) does not contain a tissue region and hence, the top-left 40× tile is not processed for analysis.

Figure 11:
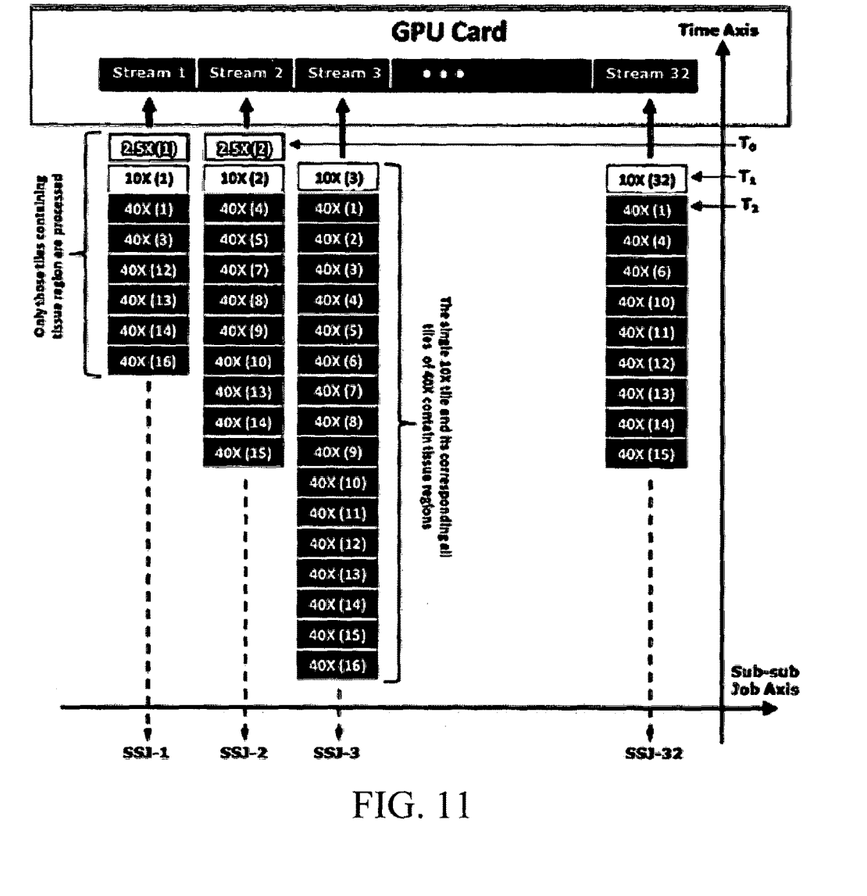
FIG. 11 depicts an arrangement of data to be executed by 32 parallel streams on a GPU as a part of sub-job computation process.

FIG. 11 depicts an arrangement of data to be executed by parallel streams on a GPU as a part of sub-job computation process. All tiles executed by a stream (from 2.5×, 10× or 40×) correspond to a sub-sub-job. There are 32 sub-sub-jobs of a sub-job, each getting executed in parallel with other sub-sub-jobs of the sub-job.

Further, different organs have different scheduling requirements. For example, a rat's kidney needs to be processed with 40× tiles of a sub-job before the corresponding parent 10× tiles and grandparent 2.5× tiles. The order of priority for processing an image resolution for a segment of a multi-resolution medical image depends on an intrinsic image processing and machine learning algorithms used for each organ. Thus, the order of priority for processing an image resolution for a segment of a multi-resolution medical image varies. System 104 handles all permutations of image resolution changes.

After executing each sub job associated with the multi-resolution medical image, a result sub-job is created and inserted into the global job array. The result sub-job corresponds to collating results from all the sub-jobs. The result sub-job is added as a dependent job in the queue of the global job array. Thus, the result sub-job is not executed until each sub-job associated with the multi-resolution medical image is executed. Reporting unit 208 executes the result sub-job and collates the results from each sub job associated with the result the multi-resolution medical image. Finally, display unit 210 displays a collated report for the multi-resolution medical image.

In accordance with the method and system disclosed herein, humongous multi-resolution tissue images are analyzed within few minutes for helping pathologists to evaluate effects of various drugs administered to animals for histopathological pre-clinical trials. Further, the method and system also enables parallel processing of multiple multi-resolution medical images simultaneously from multiple users. Thus, a request for multi-resolution medical image analysis can be given by multiple users simultaneously. Histology and non-histology features (like color, texture) are detected at different image resolutions in multi-resolution medical images of sizes ranging in megabytes (MBs) and gigabytes (GBs). The appropriate analysis of the multi-resolution medical images is reported in a stipulated time. In addition, the system also handles multiple requests from client computing devices and queues the jobs associated with each multi-resolution medical image based on priorities associated with each multi-resolution medical image.

The system disclosed here can be configured to be extended to perform analysis on Immuno-Histochemical (IHC) stained tissue images, fluorescent stained tissue images, genotoxic slides, clinical data and any other suitable tissue images. Further, the system can also be configured to be extended to perform analysis on Digital Imaging and Communications (DiCom) images such as, but not limited to, Magnetic resonance Imaging (MRI), Computerized Tomography (CT) scan, Positron Emission Tomography (PET) scan, and Ultra Sound.

Those skilled in the art will realize that the above recognized advantages and other advantages described herein are merely exemplary and are not meant to be a complete rendering of all of the advantages of the various embodiments of the invention.

In the foregoing specification, specific embodiments of the invention have been described. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of the invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

We claim:

1. A method of analyzing at least one multi-resolution medical image, a multi-resolution medical image being a pre-clinical histo-pathology image, the method comprising:
   receiving the at least one multi-resolution medical image of at least one tissue, wherein a tissue is a stained tissue that is treated with at least one drug;
   dividing each multi-resolution medical image into a plurality of segments, wherein each segment comprises at least one tile;
   processing each segment of the plurality of segments of each multi-resolution medical image utilizing at least one computation node, wherein each computation node comprises at least one Graphical Processing Unit (GPU);
   collating results corresponding to each segment of a multi-resolution medical image; and
   displaying a collated report corresponding to each multi-resolution image in response to collating the results corresponding to each segment of the multi-resolution image.

2. The method of claim 1, wherein the processing each segment of each multi-resolution medical image comprises:
   creating a sub job corresponding to at least one tile associated with a segment, wherein a sub job corresponds to analyzing at least one tile associated with the segment across multiple resolutions associated with the multi-resolution medical image;
   queuing each sub-job into a global job array, wherein the global job array is utilized for scheduling a sub-job; and
   scheduling each sub job at least one computation node using the global job array based on at least one of a priority associated with each sub-job and an availability status of each computation node of the at least one computation node.

3. The method of claim 2, wherein each sub-job is further divided into a plurality of sub-sub-jobs, wherein a sub-sub-job corresponds to analyzing at least one tile of the segment at an image resolution of the multiple resolutions associated with the multi-resolution medical image.

4. The method of claim 3, wherein each sub-sub-job corresponding to a multi-resolution medical image is executed in a predefined order based on a type of the tissue in the multi-resolution medical image.

5. The method of claim 3, wherein the collating results corresponding to each segment of a multi-resolution medical image comprises:
   collating analysis results corresponding to each sub-sub-job of a sub-job corresponding to a segment of a multi-resolution medical image;
   collating analysis results corresponding to each sub-job corresponding each segment of the multi-resolution medial image in response to collating analysis results corresponding to each sub-sub-job of each sub-job; and
   generating the collated report in response to collating analysis results corresponding to each sub job corresponding to each segment of the multi-resolution medial image.

6. The method of claim 1, wherein at least one multi-resolution medical image is received from at least one of a scanning device and an archived storage.

7. The method of claim 1, wherein a tissue is an animal organ.

8. A system for analyzing at least one multi-resolution medical image, a multi-resolution medical image being a pre-clinical histo-pathology image, the system comprising:
   an image acquiring unit configured to receive the at least one multi-resolution medical image of at least one tissue, wherein a tissue is a stained tissue that is treated with at least one drug;
   a processor configured to divide each multi-resolution medical image into a plurality of segments, wherein each segment comprises at least one tile;
   at least one computation node configured to process each segment of the plurality of segments of each multi-resolution medical image, wherein each computation node comprises at least one GPU;
   a reporting unit configured to collate results corresponding to each segment of a multi-resolution medical image; and
   a display unit configured to display a collated report corresponding to each multi-resolution image in response to collating the results corresponding to each segment of the multi-resolution image.

9. The system of claim 8, wherein the processor is further configured to:
   create a sub-job corresponding to at least one tile associated with a segment, wherein a sub-job corresponds to analyzing at least one tile associated with the segment across multiple resolutions associated with the multi-resolution medical image;
   queue each sub-job into a global job array, wherein the global job array is utilized for scheduling a sub-job; and
   schedule each sub-job at least one computation node using the global job array based on at least one of a priority associated with each sub-job and an availability status of each computation node of the at least one computation node.

10. The system of claim 9, wherein the processor is further configured to:
    divide each sub-job into a plurality of sub-sub-jobs, wherein a sub-sub-job corresponds to analyzing at least one tile of the segment at an image resolution of the multiple resolutions associated with the multi-resolution medical image; and
    schedule the sub-sub-job at least one computation node based on at least one of a priority associated with the sub-sub-job and an availability status of each computation node of the at least one computation node.

11. The system of claim 10, wherein the reporting unit is configured to:
    collate analysis results corresponding to each sub-sub-job of a sub-job corresponding to a segment of a multi-resolution medical image;
    collate analysis results corresponding to each sub-job corresponding each segment of the multi-resolution medial image in response to collating analysis results corresponding to each sub-sub-job of each sub-job; and
    generate the collated report in response to collating analysis results corresponding to each sub-job corresponding to each segment of the multi-resolution medial image.

12. The system of claim 8, wherein the image acquiring unit receives the at least one multi-resolution medical image from at least one of at least one scanning device, an archived storage and at least one client computing device.

13. The system of claim 12, wherein the image acquiring unit is communicatively coupled with at least one of the at least one scanning device, an archived storage and the at least one client computing device over a network.

* * * * *